(12) United States Patent
Amundsen (10) Patent No.: US 7,300,279 B2
(45) Date of Patent: Nov. 27, 2007

(54) ORTHODONTIC RETAINER ELEMENTS

(76) Inventor: Ole Christian Amundsen, Volstadveien 68 C, Stavanger (NO) N-4025

(*) Notice: Subject to any disclaimer, the term of this patent is extended or adjusted under 35 U.S.C. 154(b) by 0 days.

(21) Appl. No.: 10/275,220

(22) PCT Filed: Apr. 26, 2001

(86) PCT No.: PCT/NO01/00174

§ 371 (c)(1),
(2), (4) Date: Nov. 4, 2002

(87) PCT Pub. No.: WO01/82821

PCT Pub. Date: Nov. 8, 2001

(65) Prior Publication Data

US 2003/0124478 A1  Jul. 3, 2003

(30) Foreign Application Priority Data

May 4, 2000 (NO) .................................. 20002353

(51) Int. Cl.
*A61C 7/00* (2006.01)
(52) U.S. Cl. ......................................................... 433/18
(58) Field of Classification Search .................. 433/18, 433/11, 10, 13
See application file for complete search history.

(56) References Cited

U.S. PATENT DOCUMENTS 2,150,005 A    3/1939  McNinch
3,984,915 A   10/1976  Noble et al.
4,243,386 A *  1/1981  Kawaguchi ..................... 433/9
4,311,463 A *  1/1982  Glattly ........................ 433/18
4,508,505 A *  4/1985  Smiley et al. ................. 433/18
4,609,350 A *  9/1986  Krause ......................... 433/7

FOREIGN PATENT DOCUMENTS

DE    27 53 640 A1   6/1978
GB    2 236 953      4/1991

* cited by examiner

*Primary Examiner*—Melba Bumgarner
(74) *Attorney, Agent, or Firm*—Andrus, Sceales, Starke & Sawall, LLP (57) ABSTRACT

A dental retainer device for stabilization, so-called retention, of pairs of teeth or groups of teeth in a lower jaw and/or an upper jaws in orthodontic treatment. The retainer device is formed of a pair (2) of retainer elements, consisting of two preferably individual, but in the position of use cooperating, retainer elements (4, 6). Each of the retainer elements (4, 6) is formed in with a retainer approximal surface (16, 18), the retainer approximal surfaces (16, 18) being formed complementary relative to one another. In use, one or more pairs (2) of retainer elements is/are positioned and secured with its/their individual elements (4, 6) preferably on the inner face of a tooth (20, 22) each of a pair of adjacent teeth, so that in the position of use the retainer approximal surfaces (16, 18) bear on each other and support, possibly lock, each other. Thereby pairs of teeth or groups of teeth are stabilized while it is possible at the same time to carry out normal dental hygiene by means of a toothbrush, dental floss or toothpicks, which is otherwise difficult to carry out when known retainers are used.

17 Claims, 8 Drawing Sheets

ORTHODONTIC RETAINER ELEMENTS

TECHNICAL FIELD

This invention relates to a dental retention device, also called a dental retainer, for use in patients who have undergone orthodontic treatment, or for some other reason need to have pairs of teeth or groups of teeth retained, or stabilized, in the lower and/or upper jaw(s).

BACKGROUND OF THE INVENTION

Orthodontic treatment mainly consists of a period of active treatment and a period of inactive treatment. In the period of active treatment the teeth concerned and their connective tissues are moved to the target positions in the jaw(s). The period of active treatment is then followed by a period of inactive treatment, also referred to as the retention period, during which the teeth concerned and their connective tissues are sought to be stabilized, or retained, in the positions obtained. Therefore, in the retention period orthodontic patients must wear suitable retainers 24 hours or part of it a day for up to several years, in order thereby to ensure that the tooth positions obtained are maintained over time.

Known retainers comprise removable retainers and fixed retainers.

A removable retainer is formed essentially of plastic-based retainer plates, which are often combined with steel braces and steel clamps. Said steel components can either be used as independent retainer elements, or as securing devices or as reinforcement to brace and thereby reinforce said retainer plates. The removable retainer is used during parts of the day, which means that the patient must be instructed on the use and maintenance of the retainer.

A fixed retainer is essentially formed of orthodontic wire, also called retention wire, the wire being cut into suitable lengths and adapted for the pair of teeth or segment of teeth in question. The orthodontic wire can vary in type, including individual wire or twisted wire; in cross-section, including round, square or rectangular cross-sections; and in type of metal(s) or alloys.

The wire can either be attached directly to the teeth by a suitable dental bonding material, e.g. composite material, in the form of small lumps of glue or, as earlier, in that the wire is soldered to orthodontic strips enclosing the anchoring teeth concerned, the orthodontic strips being secured to the anchoring teeth by means of a suitable bonding material. Alternatively, the fixed retainer may be formed of an integral moulded brace, a bar, with associated fasteners, so-called retention bases, which are secured to the anchoring teeth concerned by means of suitable bonding material.

Fixed retainers are preferably used on the inside of the dental arch at the front of the lower jaw (lingually) and to a somewhat lesser extent on the inside of the dental arch at the front of the upper jaw (palatinally).

To achieve a good result by the use of a removable retainer, one is completely dependent on the patient's will and ability to cooperate and maintain the retainer correctly. Moreover, retainer plates are inaccurate in the sense that over time they do not maintain the exact tooth position, so that limited tooth setting must be counted on. Besides, the plates can be uncomfortable to wear and be prone to break easily, which makes removable retainer plates unsuitable for retention lasting several years.

The use of a fixed retainer results in disadvantages in the dental hygiene and may, when dental-hygienic means are used, lead to inadvertent breakage between tooth and bonding material. As mentioned, fixed retainers are preferably used at the front of the lower jaw, tooth positions in this region of the set of teeth normally being more unstable than other regions of the set of teeth, the lingual area at the front of the lower jaw forming at the same time the primary region of deposits of plaque and formation of tartar.

A fixed retainer extends continuously from tooth to tooth in the tooth region covered by the retainer, thus preventing normal dental-hygienic use of dental floss or toothpicks. The use of dental floss is prevented in that the dental floss cannot be inserted in a normal manner between two adjacent teeth in order to clean the tooth neck area, or the cervical area, between the teeth. When dental floss is used, the patient has to insert the dental floss underneath the retention wire, an action which is technically difficult to perform, and which thereby represents a practical disadvantage. On the other hand, the use of toothpicks to clean between the teeth is easier for the patient to carry out, but the use of toothpicks may at the same time lead to serious disadvantages. When the toothpick is inserted between the teeth, the teeth are pushed, or expanded, away from each other to some degree, so that the applied expansion force stretches the retention wire(s) and stresses the anchoring points of the wire(s). The bonding material between the wire(s) and the teeth may thereby break and come loose, so that the entire retainer, or parts of it, come(s) loose from the teeth that are sought to be stabilized. Moreover, the use of toothpicks in children and juveniles may cause damage to the hard and soft tissues and is therefore not recommended for this group of patients.

When fixed retention wires are used, the desired tooth positions are secured best when the wire is glued to each tooth in the involved group of teeth, or retention segment, which is sought to be stabilized. However, it is often the case that the retention wire comes loose from one or more of the anchoring points, and this may be difficult to discover for both the patient and the dentist. Often this will not be discovered until the teeth concerned have moved away from the desired tooth positions, to a larger or smaller degree. This results in an immediately poorer result of treatment and a much poorer long-term prognosis for the stabilization of the occlusion.

A retention wire is normally secured to a tooth by means of a composite material. This is carried out in such a way that sufficient amounts of composite material are applied round the retention wire and on the surfaces of the individual anchoring teeth, and so that after hardening, the composite material appears as lumps of glue of varying extent and projection on the dental surfaces. This represents a further drawback, as the surfaces of the glue lumps, which are somewhat porous and rough, form surfaces that are suitable for plaque to accumulate on and subsequently tartar to form.

The disadvantages connected to reduced hygienic accessibility and fixed retainers inadvertently coming loose, increase in adult patients, in whom the requirements to good dental hygiene and long-term retention are stricter than what is normally the case in children and juveniles.

BRIEF SUMMARY OF THE INVENTION

The object of the invention is to provide a dental retention device, which is to ensure, in addition to stabilizing pairs of teeth and/or groups of teeth, so-called retention segments, better and easier access for dental cleaning of the cervical area between the teeth, for example by the use of a toothbrush, dental floss or toothpicks. At the same time the retention device is to prevent or reduce the risk of breakage of the bonding material between the retainer and the retention segment, so that the retainer does not separate from the teeth which are sought to be stabilized, and to prevent or reduce other drawbacks of known technique.

The object is realized through the use of so-called retainer elements in the form of one or more pairs of orthodontic retainer elements. A pair of retainer elements is formed of two retainer elements, preferably individual but cooperating in their positions of use, the pair of elements being secured preferably on the lingual, possibly the palatine, surface of two adjacent teeth in a dental arch, one retainer element thereof for each adjacent tooth, and so that in its position of use one element abuts and touches the other element along vertical or approximately vertical side surfaces, or so-called retainer approximal surfaces. In a pair of retainer elements the retainer approximal surface of one element is formed complementary to the retainer approximal surface of the other element, so that in the position of use these contact surfaces are bearing on each other, completely or partially. In addition the retainer approximal surfaces may possibly be surface-treated, so that the surfaces are formed and/or adapted with a desired degree of roughness, as possible relative movements of the surfaces provide a desired degree of friction when, in the position of use, they are forced, and thereby exert a compressive force, against each other. When positioned naturally in their balanced positions in connective tissues, adjacent teeth may exert a certain compressive force on each other (physiological migration), this compressive force being transmitted by the bonding agent and the pair of retainer elements to the retainer approximal surfaces of the pair of elements. This compressive force may for example be increased in that one element of a pair of elements is formed with a magnet, which cooperates, in the position of use, with a magnet formed in the other element, the two magnets being of opposite polarity, so that they attract one another, and the magnets preferably being placed inside the elements.

The pair of retainer elements is preferably placed inside the dental arch, so that that the retainer approximal surfaces correspond with and overlap the tooth approximal surfaces of the adjacent pair of teeth, preferably so that the retainer approximal surfaces of the pair of elements are parallel to the tooth approximal surfaces of the adjacent pair of teeth and possibly the longitudinal axes of the adjacent teeth. In this way dental floss, for example, may be inserted between the tooth approximal surfaces of the adjacent pair of teeth, and thereby be inserted at the same time between the retainer approximal surfaces of the pair of elements behind.

In the position of use each retainer element is formed moreover of one basal surface and one outer surface. The basal surface forms the securing area of the element to the dental surface, the basal surface possibly being plane or rounded. The outer surface of the element faces freely inwards towards the oral cavity and my be touched by the tongue, which involves that the outer surface should with advantage be polished smooth and in the central region of the surface possibly be formed with a suitable rounding with the aim that the retainer elements should be experienced, to the greatest degree possible, as comfortable for the patient to use.

A retainer element may vary both in size and shape, depending on the patient's dental relations and needs. Common is though, that in its external dimensions the retainer element is smaller than, and preferably considerably smaller than, the corresponding dimensions of the tooth surface that the element is secured to. Seen in a plan view towards the dental surfaces, and possibly also in a side view, and placed in its position of use on the dental surfaces of a pair of adjacent teeth, the outer surface of a pair of retainer elements may for example take an elliptical or ellipse-like circumferential shape, possibly a rounded rectangular shape. In addition the pair of retainer elements is divided into two preferably equal, or approximately equal, cooperating individual elements, the pair of elements preferably being divided along, or approximately along, a plane through the smallest diametric axis of the elliptical or ellipse-like circumferential shape. In its position of use, the pair of elements preferably takes its largest thickness in the central region at the retainer approximal surfaces of the elements, so that in this region the pair of elements projects the most from the dental attachment surface, the pair of elements moreover being formed with a gradually decreasing thickness in preferably a radial, or approximately radial, direction towards the circumferential line of the pair of elements.

The cooperating and complementary retainer approximal surfaces of the pair of retainer elements could vary in configuration depending on the concerned patient's dental relations and needs. For example, the retainer approximal surface of each element may be formed plane (two-dimensional), so that in its position of use the pair of elements is formed of two adjacent surfaces positioned parallel against one another. Also, the retainer approximal surface of one element may be formed by several non-parallel plane surface segments, whereas the retainer approximal surface of the other and adjacent element is formed with an equal number of complementary and non-parallel plane surface segments. As an alternative, possibly as a supplement, the two retainer approximal surfaces may be formed complementary in the three-dimensional plane by means of undulated or wavy and/or curved and/or corrugated surfaces, the retainer approximal surface of one element thereby being formed for example with a convex curvature, whereas the retainer approximal surface of the other and adjacent element is formed with a complementary concave curvature. Moreover, various such configurations of complementary retainer approximal surfaces are shown in the following exemplary embodiments.

Common for all such different configurations of the retainer approximal surfaces of pairs of elements is that because of their complementary geometric configurations they cooperate in their positions of use in the way that they mutually support, possibly lock, each other and thereby have a stabilizing effect on each other. If, during the retention period, one tooth seeks to divert from the desired tooth position, either in that the tooth seeks to rotate about its own longitudinal axis and/or that the tooth rotates about its anchoring area in the connective tissue in the tooth gum, the adjacent tooth will seek to resist this through the pair of retainer elements. In addition such undesired tooth movements can be counteracted in that cooperating retainer approximal surfaces are formed and/or adapted with a desired degree of roughness, so that the friction that occurs when the retainer approximal surfaces are forced against one another, counteracts this diversion motion. This counteracting effect is further increased in that all the teeth in a retention segment can be provided successively and in pairs with cooperating pairs of retainer elements, so that the retention segment is thereby stabilized by means of several such pairs of retainer elements. Therefore, every tooth in the retention segment is provided with two retainer elements, one element thereof at each of the two tooth approximal surfaces of the tooth, the connection between the two retainer elements being formed, in terms of strength, by the tooth itself. Thereby, these two retainer elements do not form a pair of complementarily cooperating retainer elements. On the contrary, each of the two elements is arranged to a complementary and cooperating element on an adjacent tooth.

The positioning of a pair of retainer elements on the adjacent teeth in question may for example be carried out by means of a so-called applicator strip or guide strip, a pair of retainer elements being releasably attached to the guide strip. The guide strip has a given thickness utilized during use in that the guide strip is inserted between the tooth approximal surfaces of two adjacent teeth, these surfaces normally being positioned entirely or partially in contact with each other, and thereby the adjacent teeth are pushed away from each other within the physiological mobility limits of the teeth. While the guide strip is still positioned interdentally, the guide strip and the releasably attached pair of retainer elements are subsequently pulled in towards the dental attachment area. In this phase the three-dimensional positioning of the retainer elements can possibly be adjusted further relative to the dental surface and possibly relative to each other through adjustment of the applied amount and the positioning of bonding agent, for example composite material, so that after hardening, the bonding agent will form a firm layer of bonding agent of a desired three-dimensional distribution thickness. By means of known techniques for the bonding between the element material, for example metal or porcelain, and the bonding material, and between the teeth and the bonding material, a strong bonding between the elements and the teeth is ensured. The attachment areas of the elements against the dental surfaces may be affected in that their basal surfaces are provided with a suitable configuration and/or surface treatment, for example sandblasting of some form. After the bonding agent has hardened, the guide strip is detached from the retainer elements and removed. Thereby the adjacent teeth will naturally seek back, or draw together, into the previous balanced position. This together-pulling force which is released on the removal of the guide strip, will also be transmitted through the teeth and the hardened bonding agent to the retainer elements and their retainer approximal surfaces, so that these surfaces are forced towards each other in the same manner as that, in which the tooth approximal surfaces of the two adjacent teeth are forced together. This together-pulling force, which is released on removal of the guide strip, and which provides, together with the roughness of the surfaces the desired degree of friction between the surfaces, can be adjusted by using a desired thickness for the guide strip. A thick guide strip will push the teeth further apart than a thin guide strip, so that the thick guide strip will finally effect a greater together-pulling force than a thin guide strip.

In addition to stabilizing pairs of teeth or groups of teeth in the lower jaw and/or the upper jaw, the use of retainer elements in the form of at least one pair of retainer elements will also ensure a high level of dental hygiene in the retention period of orthodontic treatment, as good access for a toothbrush, possibly dental floss or toothpicks, is achieved, so that i.a. the development of caries, plaque and tartar is prevented.

By means of the retainer elements the risk that the dental retainer comes loose from the dental surface during the retention period, will additionally be avoided or considerably reduced. On the other hand, should a retainer element come loose, it will be substantially easier for the patient or dentist to discover in an early phase, than what is often the case by the use of known retainers. Thereby there is also a possibility of correcting the problem early, so that the retained teeth do not have a chance to divert substantially from the target tooth positions, consequently improving the prognosis of the orthodontic treatment.

By the application of a guide strip a pair of retainer elements can be positioned precisely and quickly on the teeth in question, this for example as opposed to the time-consuming, and to the patient often uncomfortable, work operation which has to be carried out during adaptation of orthodontic wire, or retention wire, in which the wire is cut into suitable lengths and adapted to the pairs of teeth or groups of teeth in question. In the retention period the patient may moreover find the retainer elements more comfortable to wear than to wear retention wire.

BRIEF DESCRIPTION OF THE DRAWINGS

In the following part of the description and with reference to the FIGS. 1-18, different non-limiting exemplary embodiments of retainer elements and pairs of retainer elements will be shown, and also a method of placing them on the dental surface concerned, one particular reference numeral referring to the same detail in all the drawings in which this detail is represented, FIGS. 1-4 showing a pair of retainer elements, ellipse-shaped in a plan view, the two retainer elements of the pair being shown in a joined position, the elements cooperating with each other in that the retainer approximal surfaces of the elements are formed complementary to one another, so that in the joined position the elements match one another complementarily, each figure showing, in a plan view, a projection of the outer and visible joining line that appears when two complementary approximal retainer surfaces are placed cooperatingly against each other.

DETAILED DESCRIPTION OF THE INVENTION

Equipment and/or arrangement for dental treatment not concerning the invention itself directly, but otherwise being necessary for practicing the invention, is not specified any further or described in further detail in the following exemplary embodiment.

A pair 2 of retainer elements is formed of a retainer element 4 and a retainer element 6, cooperative in the position of use. Each retainer element 4 and 6 is formed of an outer surface, 8 and 10, respectively, and a basal surface, 12 and 14, respectively, and of a so-called retainer approximal surface 16 and a complementarily shaped retainer approximal surface 18. Correspondingly, a pair of adjacent teeth, a tooth 20 and 22, respectively, is formed of one tooth approximal surface 24 and one adjacent tooth approximal surface 26 and dental attachment surfaces, 28 and 30, respectively, the teeth being anchored in the connective tissues 32 of the tooth jaw. The retainer elements 4 and 6 are positioned and secured/glued to the dental attachment surfaces 28 and 30 by means of a dental bonding agent, for example composite material, and in the form of an adjusted layer 34 of bonding agent.

Figure 1:
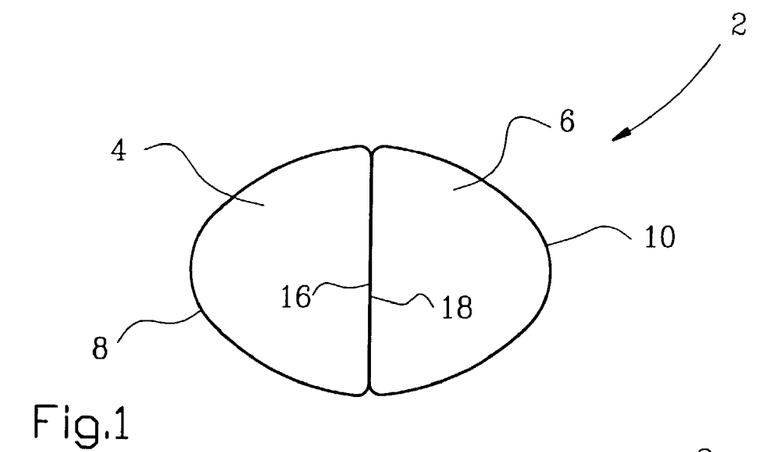
Figure 2:
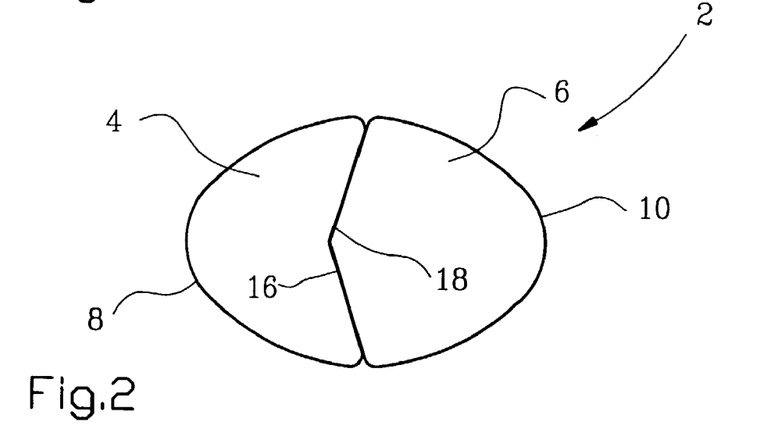
Figure 3:
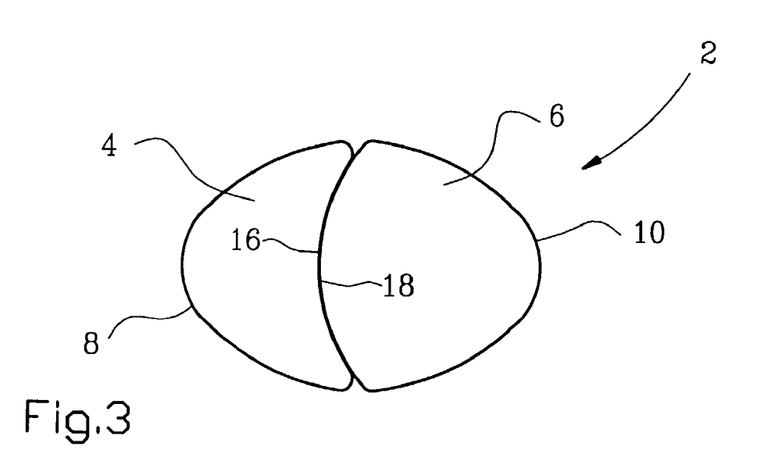
Figure 4:
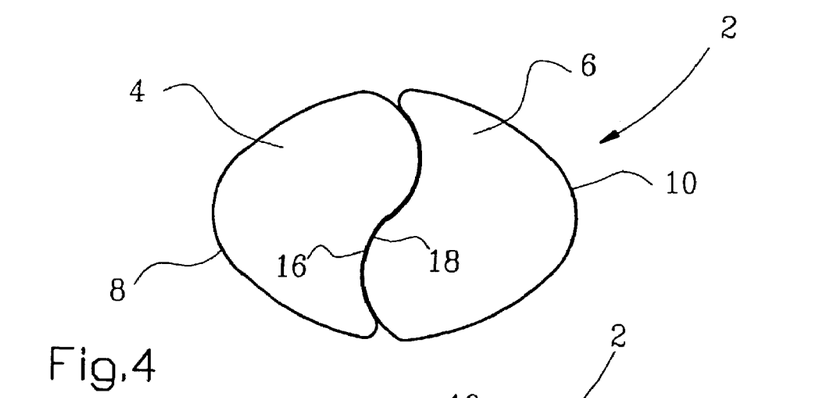
Figure 5:
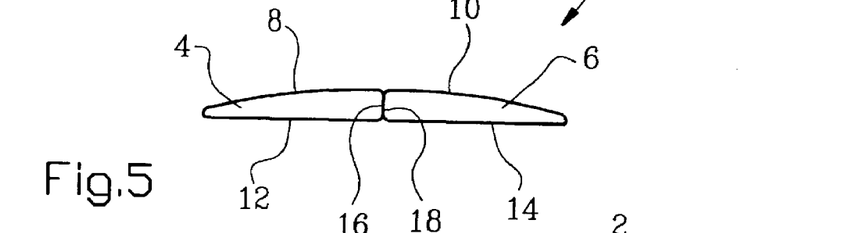
FIGS. 5-7 showing side views of a pair of retainer elements, ellipse-shaped in a plan view, for example like the pair of elements shown in FIGS. 1-4, each of the FIGS. 5-7 visualizing in a side view, and in a manner corresponding to that of FIGS. 1-4, a projection of the outer and visible joining line that appears when the two complementary retainer approximal surfaces are placed cooperatingly against each other.
Figure 6:
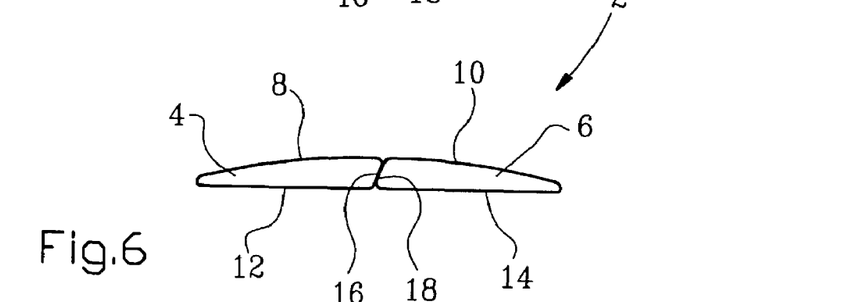
Figure 7:
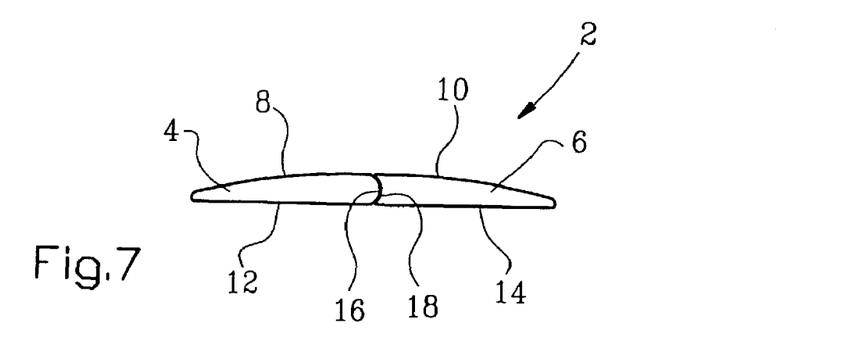
Figure 8:
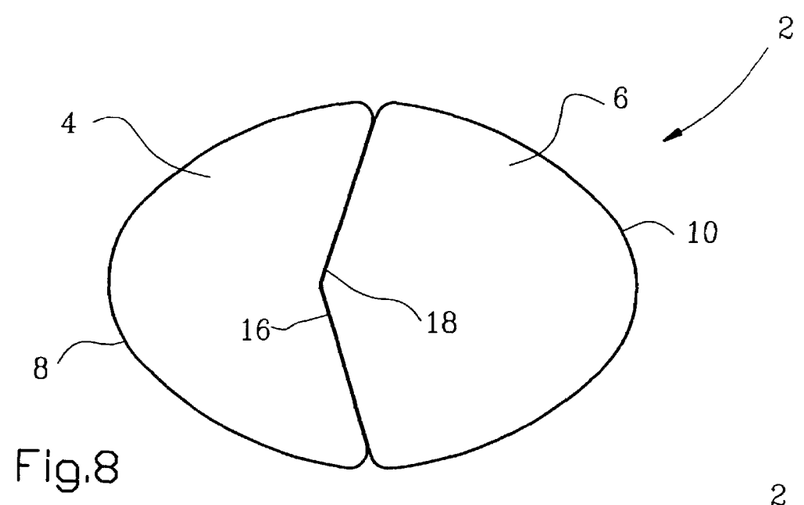
FIG. 8 showing a plan view, but on a larger scale, of the same ellipse-shaped pair of retainer elements as that shown in a joined position in FIG. 2.
Figure 9:
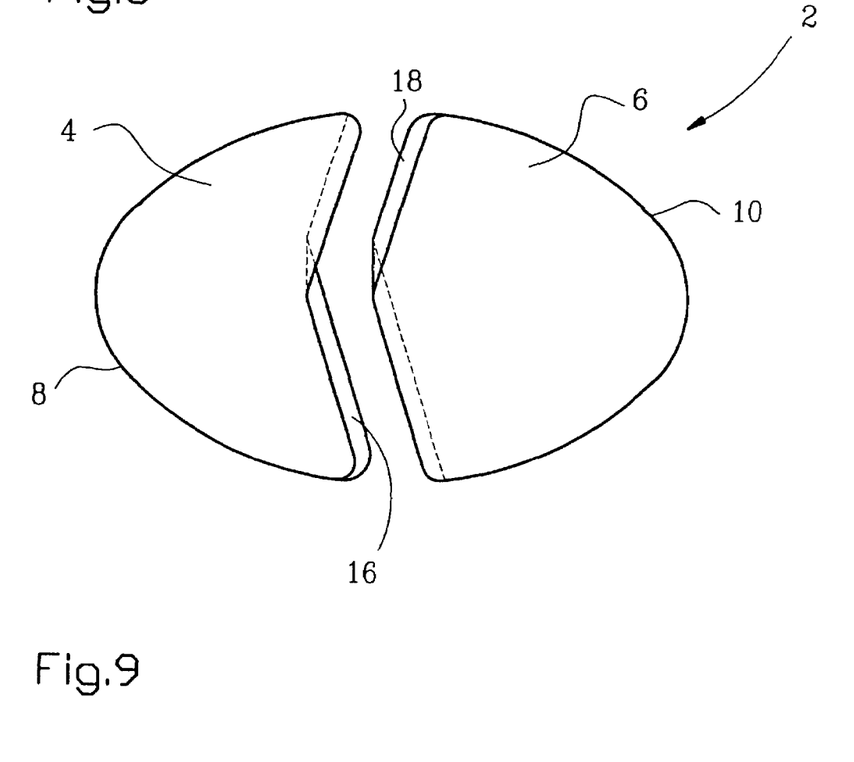
FIG. 9 also showing a plan view of the pair of retainer elements shown in FIG. 8, but the two elements in the pair being shown pulled apart, so that the two complementary retainer approximal surfaces of the elements can be visualized.

As shown in FIGS. 1-4 a pair 2 of retainer elements may for example, and not necessarily, be ellipse-shaped in a plan view, but the external surfaces 8 and 10 of the elements 4 and 6 should be formed to a great degree with a smooth and even shape, which is experienced in a retention period as easy to clean and comfortable to wear for a patient. In the position of use the surface configuration is also of importance in terms of strength, as possible breakages are more easily initiated in rough and uneven, possibly angular surface areas. The exemplary side views of the above-mentioned ellipse-shaped pair 2 of retainer elements shown in FIGS. 5-7, visualize different geometric configurations of the projection of the elements' 4 and 6 complementary retainer approximal surfaces 16 and 18 visible in a side view. However, it is evident that the complementary retainer approximal surfaces 16 and 18 of the elements 4 and 6 can be formed with any one of the configurations shown in plan views in FIGS. 1-4 combined with any one of the side view configurations shown in FIGS. 5-7, so that the complementary retainer approximal surfaces 16 and 18 may for example take surface configurations as shown in FIG. 9.

Figure 10:
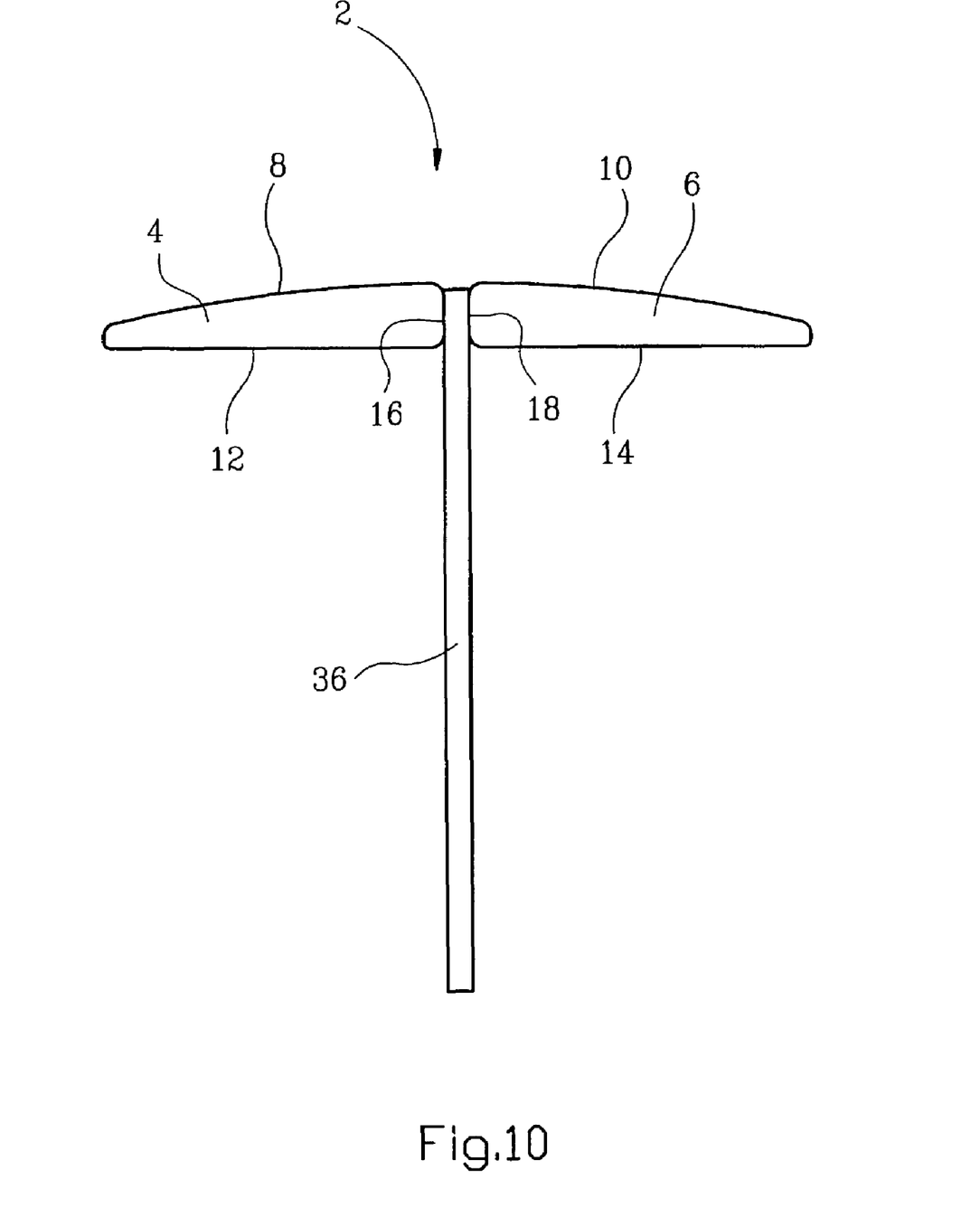
FIG. 10 showing a side view of the pair of retainer elements shown in FIG. 5, but with each of the two elements of the pair of retainer elements releasably attached on either side of a guide strip.
Figure 11:
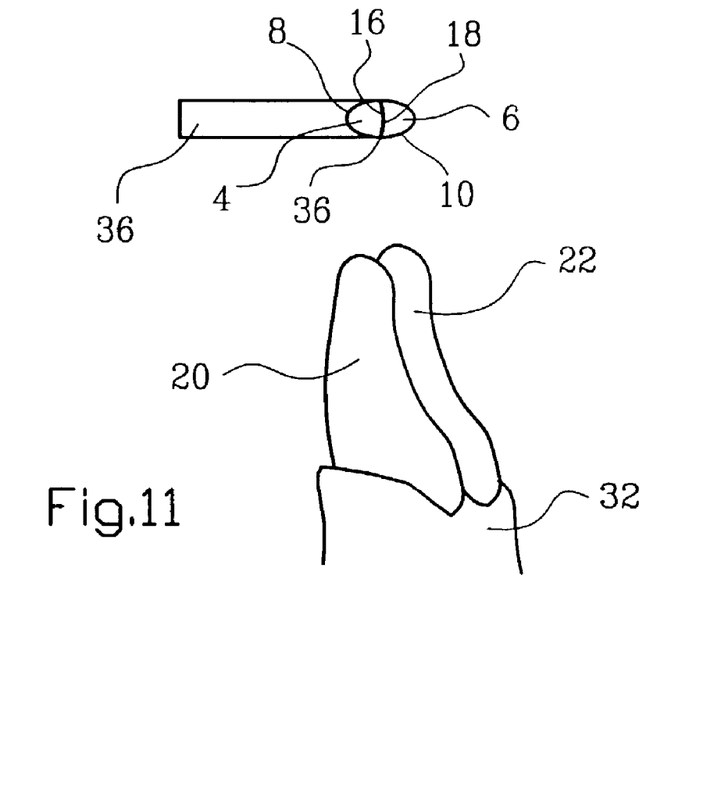
FIGS. 11-14 showing a series of perspective views of how a pair of retainer elements attached to a guide strip can be placed lingually on a pair of adjacent teeth.
Figure 12:
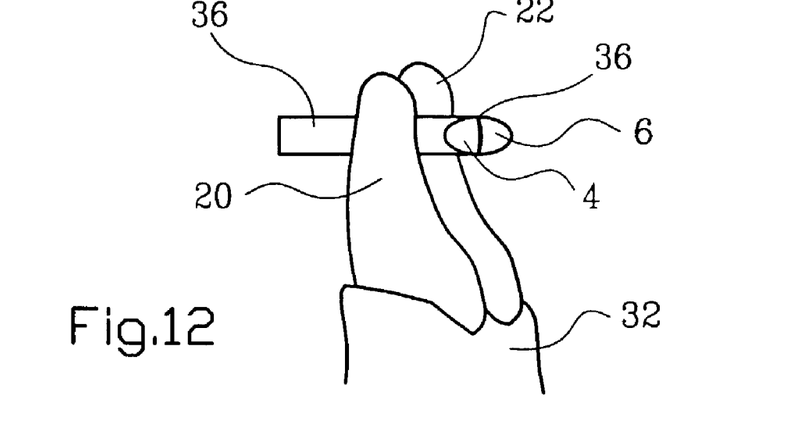
Figure 13:
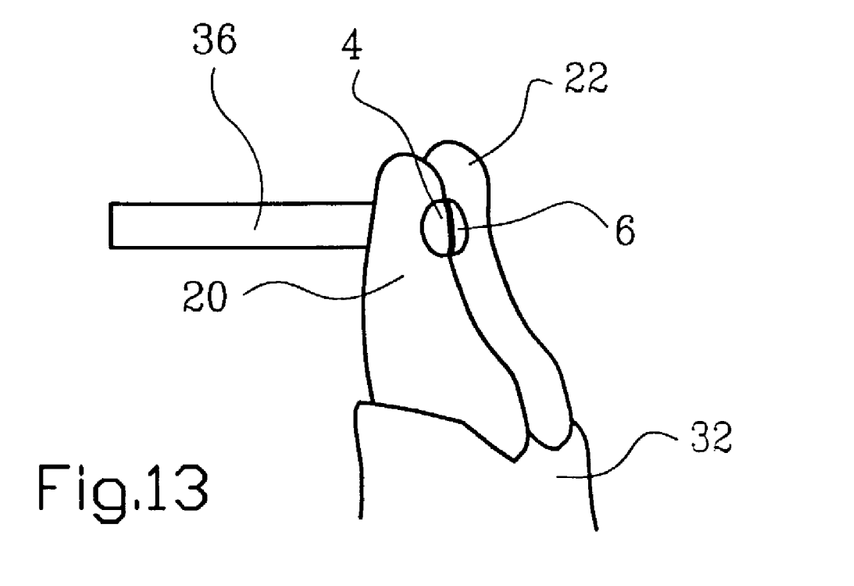
Figure 14:
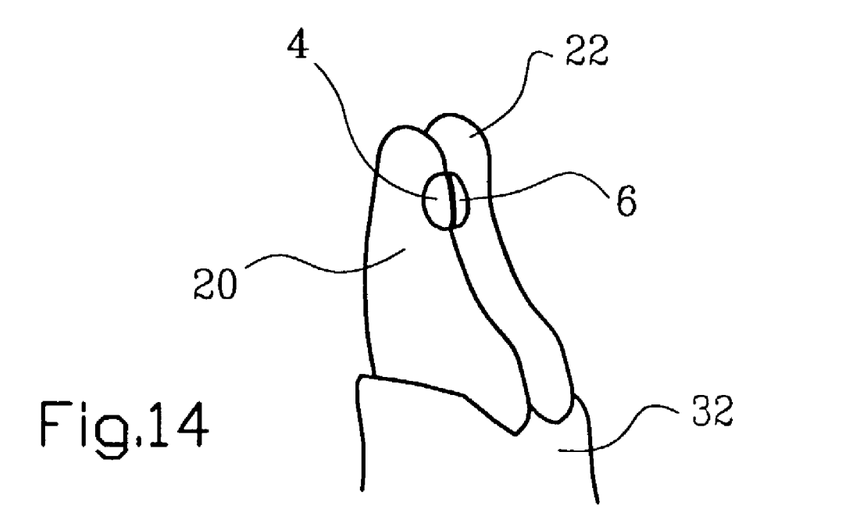

As shown in FIGS. 11-14 a pair 2 of retainer elements may be placed lingually and/or palatinally on a pair of adjacent teeth, for example by means of a guide strip 36, each retainer element 4 and 6 being releasably attached to the guide strip 36, cf. FIG. 10 and FIG. 11. As shown in FIG. 12, the guide strip 36, which has a given thickness, is inserted with the attached pair 2 of retainer elements between the tooth 20 and tooth 22 (the pair of adjacent teeth), the teeth 20 and 22 thereby being pushed apart. In this position the guide strip 36 is then displaced until each of the retainer elements 4 and 6 almost bears on a respective tooth 20 and 22 and their respective dental attachment surfaces 28 and 30, cf. FIG. 13, the bonding agent already having been applied to the basal surfaces 12 and 14 of the elements 4 and 6 and possibly to the attachment surfaces 28 and 30, so that a layer 34 of bonding agent is thereby created. After the bonding agent 34 has hardened, the guide strip 36 is then detached and removed from the elements 4 and 6, which thereby causes the teeth 20 and 22 to be brought back into their balanced positions, in which the tooth approximal surface 24 abuts the adjacent tooth approximal surface 26, the retainer approximal surface 16 of the element 4 also being brought to bear on the adjacent and complementarily shaped retainer approximal surface 18 of the element 6, cf. FIG. 14 and FIGS. 16-18.

Figure 15:
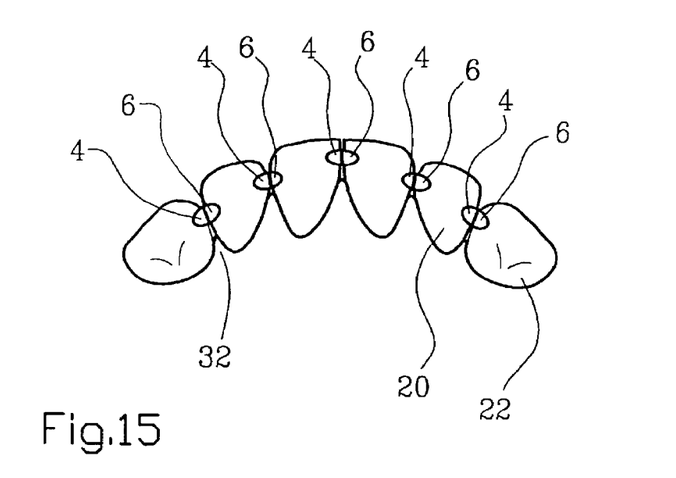
FIG. 15 shows a plan view of several cooperating pairs of retainer elements placed in the position of use on the inside of the dental arch (lingually) of the lower jaw, the pairs of retainer elements thereby stabilizing the teeth in the retention segment in question.
Figure 16:
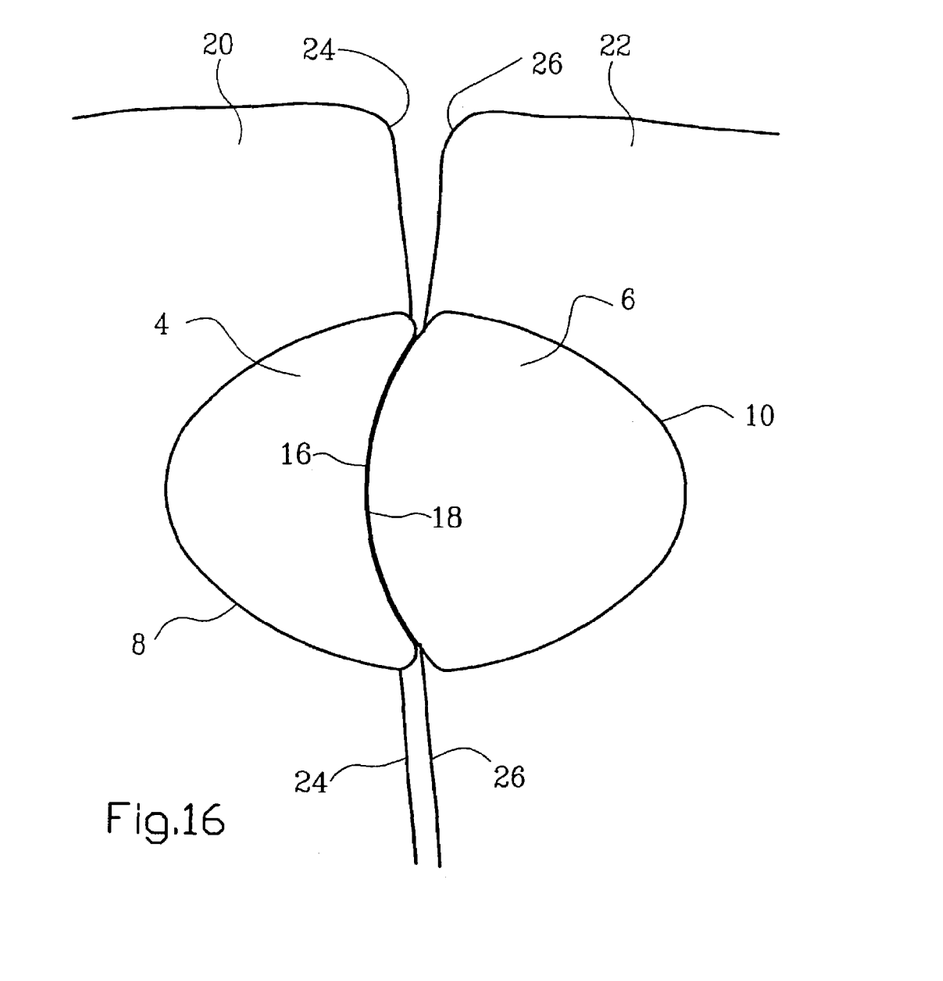
FIG. 16 showing a plan view, on a larger scale, of a sectional area of the retention segment indicated in FIG. 15, one pair of retainer elements being placed cooperatively in its position of use with one element on an adjacent tooth each, the complementary retainer approximal surfaces of the elements being placed in contact with each other.
Figure 17:
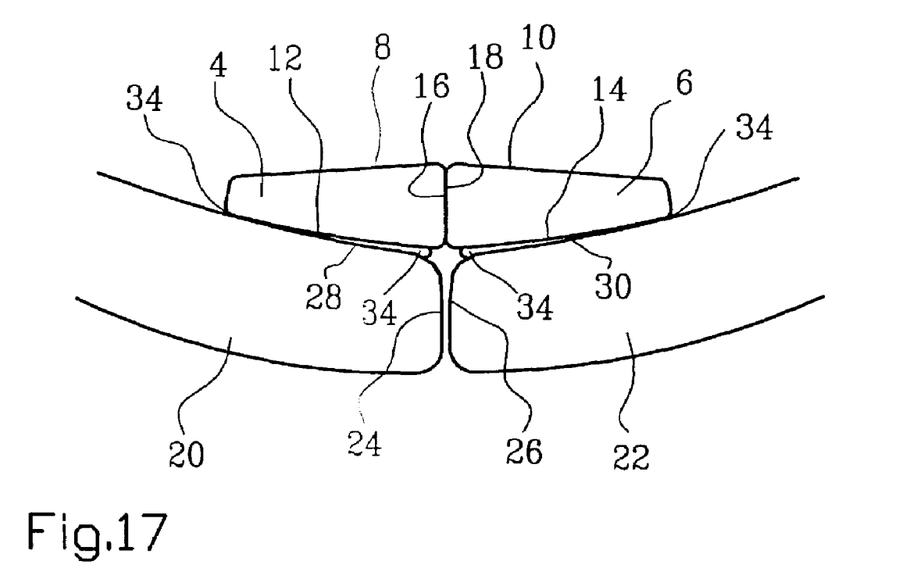
FIG. 17 showing a side view of the same sectional area as that shown in FIG. 16, the basal surfaces of the retainer elements being moderately rounded/curved, as opposed to the other side views in the drawn figures.
Figure 18:
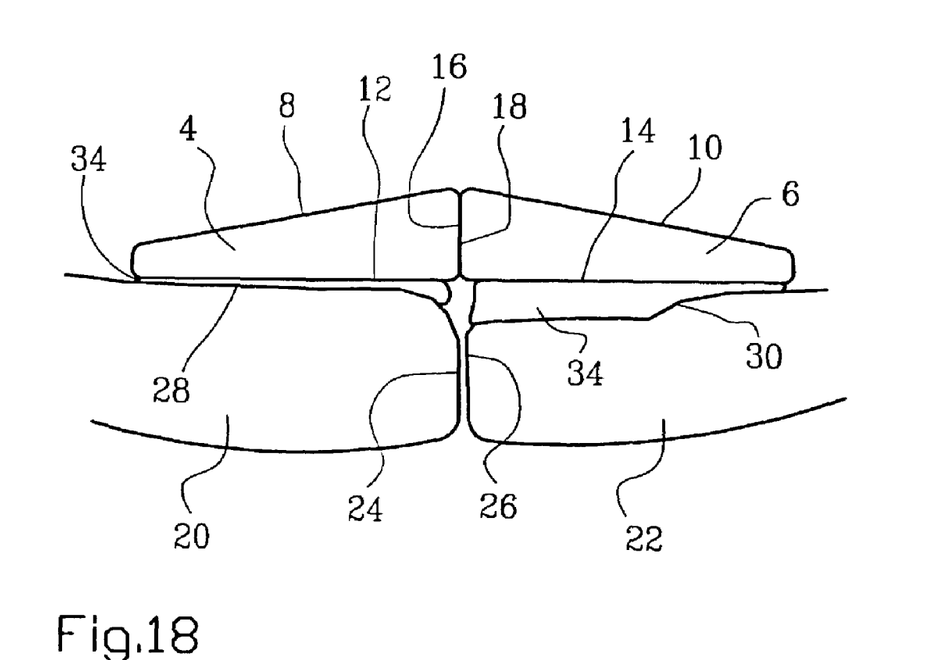
FIG. 18 showing, similarly to FIG. 17, a side view of a corresponding sectional area, the basal surfaces of the retainer elements in this case being formed plane and in their positions of use being glued in the same plane, proximity differences of retainer elements and attachment surfaces of associated teeth being equalized by application of dental bonding agent in amounts adjusted according to the prevailing proximity difference.

In practice there is normally a need to retain, or stabilize, groups of teeth, or a retention segment, in the lower and/or upper jaw(s). Thereby it may be relevant to use several such pairs 2 of retainer elements, for example as shown in FIG. 15, wherein several such cooperating pairs 2 of retainer elements are placed in their positions of use on the inside of the dental arch (lingually) in the lower jaw, so that the pairs 2 of retainer elements thereby stabilize the teeth in the retention segment in question.

The stabilizing of each pair of adjacent teeth in a retention segment is maintained in that the retainer approximal surfaces 16 and 18 of the pair 2 of elements are formed complementary, and are possibly formed with a desired degree of roughness. Because of the complementary shape the surfaces 16 and 18 cooperate in the position of use, in the way that they mutually support, possibly lock, each other, an effect which can be increased because of the friction caused by possible rough surfaces 16 and 18. If, for example, the tooth 20 seeks to divert from the desired tooth position during the retention period, either in that the tooth 20 seeks to rotate about its own longitudinal axis and/or that the tooth 20 rotates about its anchoring area in the connective tissues 32, the adjacent tooth 22 will counteract this relative movement through the pair 2 of retainer elements. The stabilizing effect is further increased in that all the teeth in a retention segment are provided, successively and in pairs, with pairs 2 of cooperating retainer elements.

The invention claimed is:

1. A dental retainer apparatus for stabilization, so-called retention, of pairs of teeth or groups of teeth belonging to at least one of a lower jaw and an upper jaw during a retention period of orthodontic treatment, wherein the retainer apparatus comprises two individual retainer elements collectively forming a pair of such elements, said pair of retainer elements intended to cooperate through mutual contact when in position of use, in which position each retainer element is individually secured to a corresponding dental attachment surface of two adjacent teeth in a dental arch; wherein each individual retainer element comprises an outer surface, a basal surface and a retainer approximal surface; and wherein said retainer approximal surfaces are provided with complementary surface shapes to one another, thereby providing mutual contact surfaces that cooperate to stabilize one another when in position of use, hence also stabilizing the associated pair of teeth to which they are attached; and wherein said retainer approximal surfaces are provided with rough surfaces to enhance friction between said pair of retainer elements when in position of use.

2. A dental retainer apparatus for stabilization, so-called retention, of pairs of teeth or groups of teeth belonging to at least one of a lower jaw and an upper jaw during a retention period of orthodontic treatment, wherein the retainer apparatus comprises two individual retainer elements collectively forming a pair of such elements, said pair of retainer elements intended to cooperate through mutual contact when in position of use, in which position each retainer element is individually secured to a corresponding dental attachment surface of two adjacent teeth in a dental arch; wherein each individual retainer element comprises an outer surface, a basal surface and a retainer approximal surface; and wherein said retainer approximal surfaces are provided with complementary surface shapes to one another, thereby providing mutual contact surfaces that cooperate to stabilize one another when in position of use, hence also stabilizing the associated pair of teeth to which they are attached; and wherein the retainer elements in a pair thereof are releasably attached on either side of a guide strip that is intended for inserting between said adjacent teeth for subsequent securing of the elements thereto.

3. A dental retainer apparatus for stabilization, so-called retention, of pairs of teeth or groups of teeth belonging to at least one of a lower jaw and an upper jaw during a retention period of orthodontic treatment, the retainer apparatus comprising:
two separate and individual retainer elements collectively forming a pair of retainer elements, said pair of retainer elements cooperating through mutual contact when in a position of use, in which position each retainer element is individually secured to a corresponding dental attachment surface of two adjacent teeth in a dental arch;
wherein each individual retainer element comprises an outer surface, a basal surface and a retainer approximal surface; and
wherein said retainer approximal surfaces are provided with complementary surface shapes to one another and comprise mutual contact surfaces that compressively abut each other, when in a position of use, and lock each other to prevent any movement of the approximal surfaces relative to each other, thereby stabilizing the retainer elements relative to each other and also stabilizing the associated teeth to which they are attached;
wherein each retainer approximal surface comprises a plurality of non-parallel, plane surface segments and wherein the respective non-parallel plane surface segments of the approximal surfaces mate with each other when in the position of use to lock the mutual contact surfaces with respect to each other.

4. The dental retainer apparatus of claim 3, wherein each retainer approximal surface has a rough surface to enhance friction between said pair of retainer elements when in a position of use.

5. The dental retainer apparatus of claim 3, wherein each retainer element in a pair thereof is provided with a partial elliptical or ellipse-like circumference shape, as seen in plan view towards said dental attachment surfaces, said pair of retainer elements collectively forming an elliptical or ellipse-like circumference shape when in cooperating, mutual contact in their position of use.

6. The dental retainer apparatus of claim 3, wherein each retainer element in a pair thereof is provided with a partial rounded rectangular circumference shape, as seen in plan view towards said dental attachment surfaces, said pair of retainer elements collectively forming a rounded rectangular circumference shape when in cooperating, mutual contact in their position of use.

7. The dental retainer apparatus of claim 3, wherein the outer surface of each retainer element is smooth.

8. The dental retainer apparatus of claim 3, wherein the outer surface of each retainer element is rounded.

9. The dental retainer apparatus of claim 3, wherein the basal surface of each retainer element is planar.

10. The dental retainer apparatus of claim 9, wherein the basal surface of each retainer surface is sandblasted, hence facilitating securing thereof to the dental attachment surface.

11. The dental retainer apparatus of claim 3, wherein the basal surface of each retainer element is rounded.

12. The dental retainer apparatus of claim 11, wherein the basal surface of each retainer surface is sandblasted, hence facilitating securing thereof to the dental attachment surface.

13. The dental retainer apparatus of claim 3, wherein the basal surface of each retainer surface is sandblasted, hence facilitating securing thereof to the dental attachment surface.

14. The dental retainer apparatus of claim 3, wherein each retainer element in a part thereof is provided with a magnet, and wherein the two magnets are of opposite polarity.

15. The dental retainer apparatus of claim 3, wherein the retainer elements in a pair thereof are releasably attached on either side of a guide strip that is intended for inserting between said adjacent teeth for subsequent securing of the elements there to.

16. A dental retainer apparatus for stabilization, so-called retention, of pairs of teeth or groups of teeth belonging to at least one of a lower jaw and an upper jaw during a retention period of orthodontic treatment, the retainer apparatus comprising:
two separate and individual retainer elements collectively forming a pair of retainer elements, said pair of retainer elements cooperating through mutual contact when in a position of use, in which position each retainer element is individually secured to a corresponding dental attachment surface of two adjacent teeth in a dental arch;
wherein each individual retainer element comprises an outer surface, a basal surface and a retainer approximal surface; and
wherein said retainer approximal surfaces are provided with complementary surface shapes to one another and comprise mutual contact surfaces that compressively abut each other, when in a position of use, and lock each other to prevent any movement of the approximal surfaces relative to each other, thereby stabilizing the retainer elements relative to each other and also stabilizing the associated teeth to which they are attached;
wherein each retainer approximal surface comprises a plurality of curvilinear surfaces and wherein the respective curvilinear surfaces of the approximal surfaces mate with each other when in a position of use to lock the mutual contact surfaces with respect to each other.

17. A dental retainer apparatus for stabilization, so-called retention, of pairs of teeth or groups of teeth belonging to at least one of a lower jaw and an upper jaw during a retention period of orthodontic treatment, the retainer apparatus comprising:
two separate and individual retainer elements collectively forming a pair of retainer elements, said pair of retainer elements cooperating through mutual contact when in a position of use, in which position each retainer element is individually secured to a corresponding dental attachment surface of two adjacent teeth in a dental arch;
wherein each individual retainer element comprises an outer surface, a basal surface and a retainer approximal surface; and wherein said retainer approximal surfaces are provided with complementary surface shapes to one another and comprise mutual contact surfaces that compressively abut each other, when in a position of use, and lock each other to prevent any movement of the approximal surfaces relative to each other, thereby stabilizing the retainer elements relative to each other and also stabilizing the associated teeth to which they are attached;

wherein each retainer approximal surface is of a combined plane and curvilinear surface shape and wherein the respective plane and curvilinear surface shapes of the approximal surfaces mate with each other when in a position of use to lock the mutual contact surfaces with respect to each other.

* * * * *